(12) United States Patent
Pagoria et al.

(10) Patent No.: US 7,829,020 B2
(45) Date of Patent: Nov. 9, 2010

(54) SIMPLE, FIELD PORTABLE COLORIMETRIC DETECTION DEVICE FOR ORGANIC PEROXIDES AND HYDROGEN PEROXIDE

(75) Inventors: Philip F. Pagoria, Livermore, CA (US); Alexander R. Mitchell, Livermore, CA (US); Richard E. Whipple, Livermore, CA (US); M. Leslie Carman, San Ramon, CA (US); John G. Reynolds, San Ramon, CA (US); Peter Nunes, Livermore, CA (US); Sharon J. Shields, San Ramon, CA (US)

(73) Assignee: Lawrence Livermore National Laboratory, LLC, Livermore, CA (US)

( * ) Notice: Subject to any disclaimer, the term of this patent is extended or adjusted under 35 U.S.C. 154(b) by 329 days.

(21) Appl. No.: 12/183,210

(22) Filed: Jul. 31, 2008

(65) Prior Publication Data
US 2009/0068065 A1 Mar. 12, 2009

Related U.S. Application Data

(60) Provisional application No. 60/963,331, filed on Aug. 2, 2007.

(51) Int. Cl.
*G01N 33/22* (2006.01)
(52) U.S. Cl. .......................... 422/61; 422/58; 436/135; 436/156; 436/165; 436/166
(58) Field of Classification Search .................. 422/58, 422/61; 436/135, 156, 165, 166
See application file for complete search history.

(56) References Cited

U.S. PATENT DOCUMENTS

| 5,296,380 | A | 3/1994 | Margalit et al. |
| 5,480,612 | A | 1/1996 | Margalit et al. |
| 6,767,717 | B1 | 7/2004 | Itzhaky et al. |
| 2004/0265169 | A1 | 12/2004 | Haas et al. |

*Primary Examiner*—Lyle A Alexander
(74) *Attorney, Agent, or Firm*—Eddie E. Scott; James S. Tak

(57) ABSTRACT

A simple and effective system for the colorimetric determination of organic peroxides and hydrogen peroxide. A peroxide pen utilizing a swipe material attached to a polyethylene tube contains two crushable vials. The two crushable vials contain a colorimetric reagent separated into dry ingredients and liquid ingredients. After swiping a suspected substance or surface the vials are broken, the reagent is mixed thoroughly and the reagent is allowed to wick into the swipe material. The presence of organic peroxides or hydrogen peroxide is confirmed by a deep blue color.

23 Claims, 2 Drawing Sheets

SIMPLE, FIELD PORTABLE COLORIMETRIC DETECTION DEVICE FOR ORGANIC PEROXIDES AND HYDROGEN PEROXIDE

CROSS-REFERENCE TO RELATED APPLICATIONS

This application claims the benefit of U.S. Provisional Patent Application No. 60/963,331 filed Aug. 2, 2007 and titled "A simple, field portable colorimetric detection device for organic peroxides and hydrogen peroxide." U.S. Provisional Patent Application No. 60/963,331 filed Aug. 2, 2007 and titled "A simple, field portable colorimetric detection device for organic peroxides and hydrogen peroxide" is incorporated herein by this reference.

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to colorimetric determination of organic peroxides and hydrogen peroxide and more particularly to a simple and effective peroxide pen for the colorimetric determination of organic peroxides and hydrogen peroxide.

2. State of Technology

U.S. Pat. No. 6,767,717 issued Jul. 27, 1994 to Harel Itzhaky and Ehud Keinan for a method and kit for the detection of explosives provides the following state of technology information: "Improvised explosive devices based on peroxide containing materials have increasingly been used in recent years by various terrorist organizations, especially in Israel, as well as in the UK and the USA. The main reason is that such peroxide-based explosives can be easily "home-made" using inexpensive, readily available starting materials which can be purchased in most hardware and paint stores, even in bulk quantities . . . . Another commonly used peroxide based explosive is hexamethylenetriperoxidediamine (hereinafter "HMTD"). It can be conveniently prepared by treating hexamethylenetetramine with hydrogen peroxide in the presence of a weak acid, such as citric acid, in order to neutralize the liberated ammonia . . . . Although many peroxide containing materials of the above-described type are known for more than 70 years, no satisfactory method for their detection has been suggested to date. The detection of peroxide-based explosives is particularly difficult because all these materials do not contain nitro groups or any other nitrogen oxide functional groups. Since most of the currently available explosive detectors are based on the detection of nitro groups, they cannot be employed for detection of peroxide-based materials. Consequently, and in view of the increased use of such peroxide-based explosives by terrorists, especially in the Middle East as well as in other parts of the world, there exists an urgent need for highly sensitive methods and devices for the early detection of peroxide-based explosives and improvised explosive devices employing them."

United States Published Patent Application No. 2004/0265169 for an inspection tester for explosives provides the following state of technology information: "It is known that surfaces in contact with explosives (for example, during storage, handling, or device fabrication) will readily become contaminated with explosives particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," J. Forensic Science 27 (1982) 783; J. D. Twibell et al., "The Persistence of Military Explosives on Hands," J. Forensic Science 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosives residue will likely persist in large amounts on the explosives packaging and environs, as well as on the individuals involved in building the explosives device, which can provide an avenue for detection of the presence of explosives.

International Patent Application No. WO 2005/089058 by Shai Amisar published Sep. 29, 2005 for a method and kit for detecting explosive substances containing certain oxidants provides the following state of technology information: "In recent times, the use of home-made, improvised explosives has been growing rapidly, and peroxide based explosives, like triacetonetriperoxide (TATP) and hexamethylenetriperoxidediamine (HMTD), have been shown to be easily manufactured and almost as strong as the standard explosives used today. Methods and tests kits for detecting explosives selected from nitroaromatics, organic nitrates, nitramines, inorganic nitrates, chlorates and bromates, have been described by Margalit in U.S. Pat. Nos. 5,296,380 and 5,480,612. Neither of these patents describe detection of peroxide based explosives. Itzhal et al, in W0 99/43846, has described a method and kit for detecting an organic peroxide-based explosive in a sample. The organic peroxide is hydrolyzed with strong acid to release hydrogen peroxide, and the resulting mixture is reacted with a peroxidase enzyme and a substrate capable of being oxidized by the oxidant under the catalysis of the enzyme to produce a pronounced change in a measurable physical parameter of the substrate.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a simple and effective system for the colorimetric determination of organic peroxides and hydrogen peroxide. The present invention provides a peroxide pen utilizing a swipe material attached to a polyethylene tube containing the two crushable vials. The two crushable vials contain the calorimetric reagent separated into dry ingredients and liquid ingredients. After swiping a suspected substance or surface the vials are broken, the reagent is mixed thoroughly and the reagent is allowed to wick into the swipe material. The presence of organic peroxides or hydrogen peroxide is confirmed by a deep blue color.

The present invention enables identification of peroxide-containing explosives. It can detect peroxide-containing explosives in, e.g., unexploded ordnance, suspect explosive components, pipe bombs, and IED's. The peroxide pen 100 can be used by military, first responders, law enforcement, Transportation Department (TSA), border patrol, and forensic personnel.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figures 1, 2:
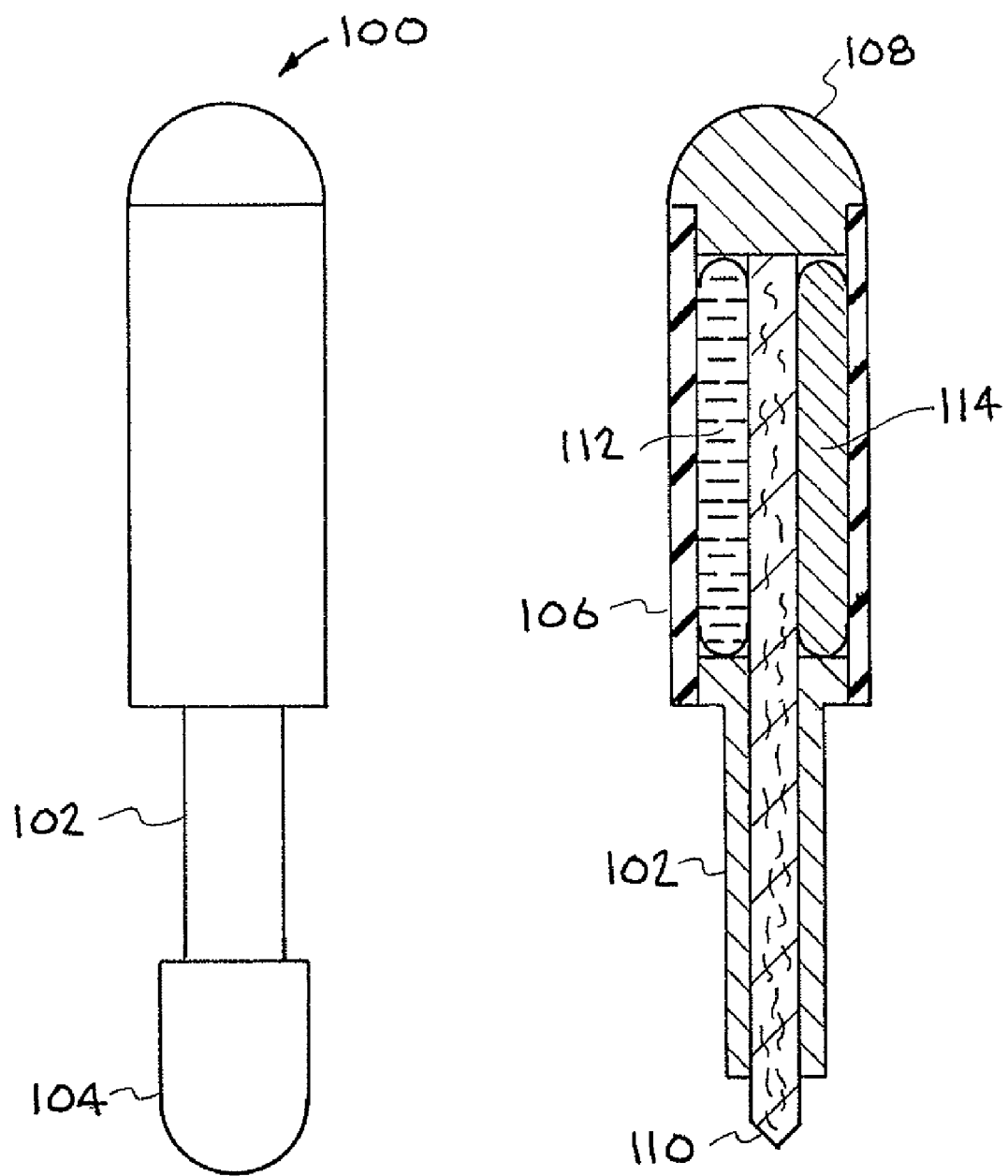
FIG. 1 illustrates one embodiment of the present invention.
FIG. 2 is a cut away view of the embodiment of the present invention illustrated in FIG. 1.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1 one embodiment of a "peroxide pen" for the colorimetric determination of organic peroxides and hydrogen peroxide is illustrated. The peroxide pen is designated generally by the reference numeral 100. The peroxide pen 100 provides a simple and effective system for the colorimetric determination of organic peroxides and hydrogen peroxide. The peroxide pen 100 comprises a swipe material that is attached to a polyethylene tube containing two crushable vials containing colorimetric reagents separated into dry ingredients and liquid ingredients. After swiping a suspected material or surface the vials are broken, the reagents mixed thoroughly and the reagents allowed to wick into the swipe material. The presence of peroxides is confirmed by a deep blue color.

The peroxide pen 100 has a peroxide pen body 102. A protective cap 104 is attached to the peroxide pen body 102. The peroxide pen 100 consists of a swipe material attached to a tube (e.g. polyethylene) that contains the colorimetric reagent in crushable vials. One vial contains the liquid components; Methanol, acetic acid, along with the 1-napthol. The other vial contains the color developer 3, iron sulfate heptahydrate and potassium disulfite. The two vials are crushed and the reagent is mixed prior to applying to the suspect explosive on the swipe material.

The peroxide pen 100 enables identification of peroxide-containing explosives. It can detect peroxide-containing explosives in, e.g., unexploded ordnance, suspect explosive components, pipe bombs, and IED's. The peroxide pen 100 can be used by military, first responders, law enforcement, Transportation Department (TSA), border patrol, and forensic personnel.

Referring now to FIG. 2 a cut away view of the peroxide pen 100 illustrated in FIG. 1 is shown. The peroxide pen 100 has a peroxide pen body 102. A swipe material 110 is attached to a tube (e.g. polyethylene) that provides the pen body 102. The protective cap 104 shown in FIG. 1 fits over swipe material 110 and the end of the pen body 102. An upper cap 108 is attached to the pen body 102.

The peroxide pen 100 contains a colorimetric reagent in crushable vials 112 and 114. The colorimetric reagent is separated into liquid ingredients and dry ingredients. The crushable vial 112 contains the liquid ingredients. The crushable vial 114 contains the dry ingredients.

The Colorimetric Reagent

The colorimetric reagent consists of a mixture of 1-napthol, $N^4$-Ethyl-$N^4$-(2-methanesulfonamidoethyl)-2-methyl-1,4-phenylenediamine sesquisulfate monohydrate (color develop 3), potassium disulfite, iron sulfate heptahydrate, methanol and acetic acid. Through Applicants' studies it was found that the colorimetric reagent is not stable and develops a blue color after about 1 week. Therefore for the peroxide pen 100 Applicants separated the solid components from the liquid components, rendering the separated mixture stable for at least 1 year. One vial, vial 112, contains the liquid components; Methanol, acetic acid, along with the 1-napthol. The other vial, vial 114, contains the color developer 3, iron sulfate heptahydrate and potassium disulfite. The two vials 112 and 11 are crushed and the reagent is mixed prior to applying to the suspect explosive on the swipe material 110.

The colorimetric reagent is fairly specific for peroxide-containing materials. It does not give a color change when exposed to 10 g of bleach (NaOCl or Ca(OCl)$_2$, perchlorates, nitrates, or nitramine, nitroaromatic or nitrate ester explosives. Some of the possible false positives include potassium chlorate {gives a deep blue color), sodium bromate, N-chlorosuccinimide and nitrite (gives a very faint blue color). The detection limit for the peroxide reagent using POREX as the swipe material is about 500 ng of TATP, as an example.

The Swipe Material

The swipe material 110 is made of an absorbent material such as POREX, glass microfibers, cellulose, nitrocellulose, filter paper, or mutli-cellular foam. Some swipe materials give a better color change than others. POREX is especially attractive because of its ability to wick liquid and concentrate the swiped unknowns. The best results are obtained when the swipe material 110 is wetted with acetonitrile (or other organic solvent) prior to swiping a suspect surface or substance, allowing the solvent to dry and then applying the colorimetric reagent. It is believed that when the POREX swipe material is wet with solvent the wicking action is inhibited and the substance is not concentrated on the tip of the POREX swipe. A dried swipe gives a much more vibrant color change.

Colorimetric Determination of Organic Peroxides and Hydrogen Peroxide

The peroxide pen 100 provides a simple and effective system for the colorimetric determination of organic peroxides and hydrogen peroxide. The peroxide pen 100 utilizes the swipe material 110 attached to the polyethylene tube 102 containing the two crushable vials 112 and 114 containing the colorimetric reagent separated into dry ingredients and liquid ingredients. After swiping a suspected substance or surface the vials 112 and 114 are broken, the reagent is mixed thoroughly and the reagent is allowed to wick into the swipe material 110. The presence of organic peroxides or hydrogen peroxide is confirmed by a deep blue color.

The peroxide pen 100 enables identification of peroxide-containing explosives. It can detect peroxide-containing explosives in, e.g., unexploded ordnance, suspect explosive components, pipe bombs, and IED's. The peroxide pen 100 can be used by military, first responders, law enforcement, Transportation Department (TSA), border patrol, and forensic personnel.

Figure 3:
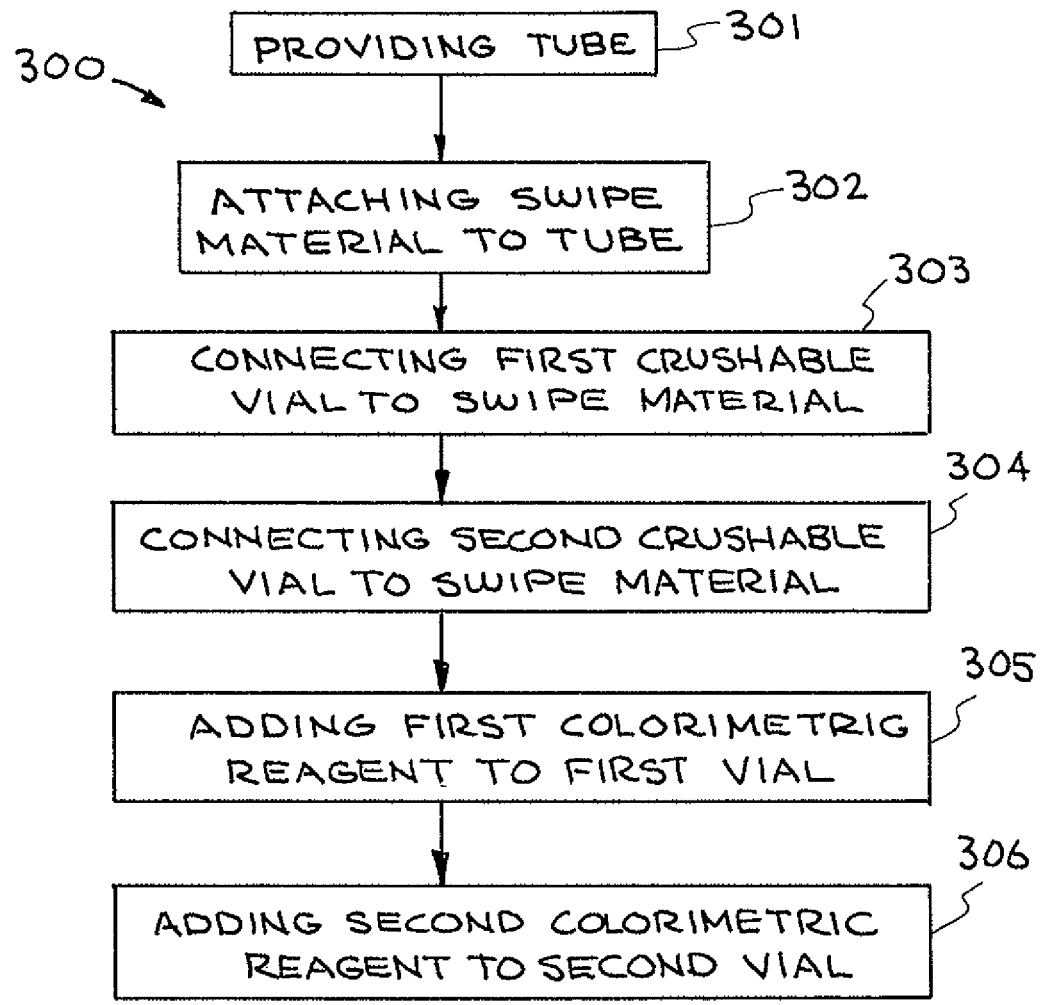
FIG. 3 is a flow chart illustrating a method of making a peroxide pen for the colorimetric determination of organic peroxides and hydrogen peroxide.

Referring to FIG. 3, a method of making a peroxide pen for the colorimetric determination of organic peroxides and hydrogen peroxide is illustrated in a flow chart. The method is designated generally by the reference numeral 300. The method 300 includes a number of steps. In one step 301 a tube is provided. The step of providing a tube comprises providing a polyethylene tube.

In another step 302 a swipe material is attached to the tube. The swipe material is made of an absorbent material such as POREX, glass microfibers, cellulose, nitrocellulose, filter paper, or mutli-cellular foam. The best results are obtained when the swipe material is wetted with acetonitrile (or other organic solvent) prior to swiping a suspect surface or substance.

In another step 303 a first crushable vial is connected to the swipe material. In another step 304 a second crushable vial is connected to the swipe material. In another step 305 a first colorimetric reagent is added to the first vial.

In another step 306 a second colorimetric reagent is added to the second vial. The first crushable vial contains the liquid components; Methanol, acetic acid, along with the 1-napthol. The second crushable vial contains the color developer 3, iron sulfate heptahydrate and potassium disulfite. The first and second vials are crushed and the reagent is mixed prior to applying to the suspect explosive on the swipe material.

Figure 4:
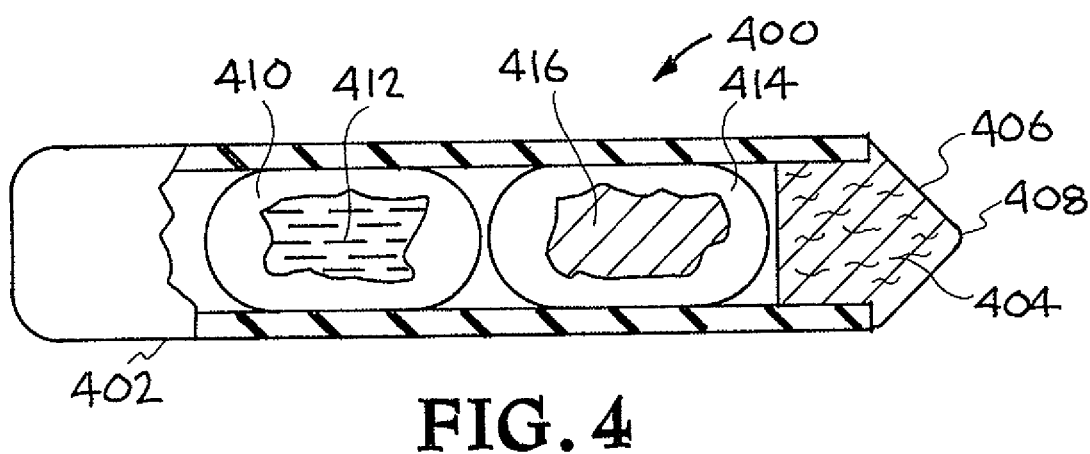
FIG. 4 illustrates another embodiment of the present invention.

Referring now to FIG. 4 another embodiment of a "peroxide pen" for the colorimetric determination of organic peroxides and hydrogen peroxide is illustrated. This embodiment of the peroxide pen is designated generally by the reference numeral 400. The peroxide pen 400 enables identification of peroxide-containing explosives. It can detect peroxide-containing explosives in, e.g., unexploded ordnance, suspect explosive components, pipe bombs, and IED's. The peroxide pen 400 can be used by military, first responders, law enforcement, Transportation Department (TSA), border patrol, and forensic personnel.

FIG. 4 provides a partially cut away view of the peroxide pen 400. The peroxide pen 400 has a peroxide pen body 402. A swipe material 404 is assembled in the tube 402 that forms the pen body 402. The peroxide pen 400 contains a colorimetric reagent in crushable vials 412 and 414. The colorimetric reagent is separated into liquid ingredients and dry ingredients. The crushable vial 412 contains the liquid ingredients 412. The crushable vial 414 contains the dry ingredients 416.

The swipe material 404 is made of an absorbent material such as POREX, glass microfibers, cellulose, nitrocellulose, filter paper, or mutli-cellular foam. Some swipe materials give a better color change than others. POREX is especially attractive because of its ability to wick liquid and concentrate the swiped unknowns. The end 408 of the swipe material 404 is tapered. The tapered end 408 forms a tip point for collecting the material to be sampled. The tapered end 408 has tip angle 406.

The peroxide pen 400 provides a simple and effective system for the colorimetric determination of organic peroxides and hydrogen peroxide. The peroxide pen 400 utilizes the two crushable vials 410 and 416 containing the colorimetric reagents separated into dry ingredients 412 and liquid ingredients 414. The peroxide pen 400 utilizes the swipe material 404 and particularly the tapered end a tip point 408 for collecting the material to be sampled. After swiping a suspected material or surface the vials 410 and 416 are broken, the reagents become mixed thoroughly and the reagents are allowed to wick into the swipe material 404. The presence of peroxides is confirmed by a deep blue color. The tapered end tip point 408 collects the material to be sampled and the mixed dry ingredients 412 and liquid ingredients 414 wick to the tapered end tip point 408. The material to be sampled and the mixed dry ingredients 412 and liquid ingredients 414 become concentrated at the tapered end tip point 408. This provides a more sensitive colorimetric determination of organic peroxides and hydrogen peroxide.

The best results are obtained when the swipe material 404 is wetted with acetonitrile (or other organic solvent) prior to swiping a suspect surface or substance, allowing the solvent to dry and then applying the colorimetric reagent. It is believed that when the POREX swipe material is wet with solvent the wicking action is inhibited and the substance is not concentrated on the tip of the POREX swipe. A dried swipe gives a much more vibrant color change.

The peroxide pen 400 enables identification of peroxide-containing explosives. It can detect peroxide-containing explosives in, e.g., unexploded ordnance, suspect explosive components, pipe bombs, and IED's. The peroxide pen 400 can be used by military, first responders, law enforcement, Transportation Department (TSA), border patrol, and forensic personnel.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for the colorimetric determination of organic peroxides and hydrogen peroxide, comprising:
   a tube,
   a swipe material attached to said tube,
   a first crushable vial in fluid communication said swipe material,
   a first colorimetric reagent comprising methanol, acetic acid and 1-napthol in said first vial,
   a second crushable vial in fluid communication said swipe material, and
   a second colorimetric reagent comprising iron sulfate heptahydrate and potassium disulfate in said second vial.

2. The apparatus for the colorimetric determination of organic peroxides and hydrogen peroxide of claim 1 wherein said tube is a polyethylene tube.

3. The apparatus for the colorimetric determination of organic peroxides and hydrogen peroxide of claim 1 wherein said first colorimetric reagent in said first vial is a liquid colorimetric reagent.

4. The apparatus for the colorimetric determination of organic peroxides and hydrogen peroxide of claim 1 wherein said second colorimetric reagent in said second vial is a dry colorimetric reagent.

5. The apparatus for the colorimetric determination of organic peroxides and hydrogen peroxide of claim 1 wherein said first colorimetric reagent in said first vial is a liquid colorimetric reagent and wherein said second colorimetric reagent in said second vial is a dry colorimetric reagent.

6. The apparatus for the colorimetric determination of organic peroxides and hydrogen peroxide of claim 1 wherein said swipe material is a porous swipe material.

7. The apparatus for the colorimetric determination of organic peroxides and hydrogen peroxide of claim 1 wherein said swipe material is a porous plastic swipe material.

8. The apparatus for the colorimetric determination of organic peroxides and hydrogen peroxide of claim 1 wherein said swipe material is a microfibers swipe material.

9. The apparatus for the colorimetric determination of organic peroxides and hydrogen peroxide of claim 1 wherein said swipe material is a cellulose swipe material.

10. The apparatus for the colorimetric determination of organic peroxides and hydrogen peroxide of claim 1 wherein said swipe material is a nitrocellulose swipe material.

11. The apparatus for the colorimetric determination of organic peroxides and hydrogen peroxide of claim 1 wherein said swipe material is a filter paper swipe material.

12. The apparatus for the colorimetric determination of organic peroxides and hydrogen peroxide of claim 1 wherein said swipe material is a mutli-cellular foam swipe material.

13. The apparatus for the colorimetric determination of organic peroxides and hydrogen peroxide of claim 1 wherein said swipe material is wetted with organic solvent.

14. The apparatus for the colorimetric determination of organic peroxides and hydrogen peroxide of claim 1 wherein said swipe material is wetted with acetonitrile.

15. The apparatus for the colorimetric determination of organic peroxides and hydrogen peroxide of claim 1 wherein said swipe material has an end with a tapered point.

16. The apparatus for the colorimetric determination of organic peroxides and hydrogen peroxide of claim 1 wherein said first crushable vial and said second crushable vial are connected to said tube on opposite sides of said tube.

17. The apparatus for the colorimetric determination of organic peroxides and hydrogen peroxide of claim 1 wherein said first crushable vial and said second crushable vial are connected to said tube with said first crushable vial above said second crushable vial.

18. A method of making a peroxide pen for the colorimetric determination of organic peroxides and hydrogen peroxide, comprising the steps of:
providing a tube,
attaching a swipe material to said tube,
connecting a first crushable vial in fluid communication said swipe material,
connecting a second crushable vial in fluid communication said swipe material,
adding a first colorimetric reagent comprising methanol, acetic acid and 1-napthol to said first vial, and
adding a second colorimetric reagent comprising iron sulfate heptahydrate and potassium disulfate to said second vial.

19. The method of making a peroxide pen for the colorimetric determination of organic peroxides and hydrogen peroxide of claim 18 wherein said step of adding a first colorimetric reagent to said first vial comprises adding a liquid colorimetric reagent to said first vial.

20. The method of making a peroxide pen for the colorimetric determination of organic peroxides and hydrogen peroxide of claim 18 wherein said step of adding a second colorimetric reagent to said second vial comprises adding a dry colorimetric reagent to said second vial.

21. The method of making a peroxide pen for the colorimetric determination of organic peroxides and hydrogen peroxide of claim 18 wherein said step of adding a first colorimetric reagent to said first vial comprises adding a liquid colorimetric reagent to said first vial and wherein said step of adding a second colorimetric reagent to said second vial comprises adding a dry colorimetric reagent to said second vial.

22. The method of making a peroxide pen for the colorimetric determination of organic peroxides and hydrogen peroxide of claim 18 including the step of wetting said swipe material with organic solvent.

23. The method of making a peroxide pen for the colorimetric determination of organic peroxides and hydrogen peroxide of claim 18 including the step of wetting said swipe material with acetonitrile.

\* \* \* \* \*